United States Patent [19]
Vong et al.

[11] Patent Number: 5,843,989
[45] Date of Patent: Dec. 1, 1998

[54] C₄-AMIDE SUBSTITUTED COMPOUNDS AND THEIR USE AS THERAPEUTIC AGENTS

[75] Inventors: Antonio Kuok Keong Vong, Sawbridgeworth; Mervyn Thompson, Harlow; John Morris Evans, Roydon; Helen Kate Ann Morgan, Sawbridgeworth, all of United Kingdom

[73] Assignee: SmithKline Beecham p.l.c., Brentford, England

[21] Appl. No.: 750,614

[22] PCT Filed: Jun. 9, 1995

[86] PCT No.: PCT/EP95/02249

§ 371 Date: Dec. 10, 1996

§ 102(e) Date: Dec. 10, 1996

[87] PCT Pub. No.: WO95/34547

PCT Pub. Date: Dec. 21, 1995

[30] Foreign Application Priority Data

Jun. 10, 1994 [GB] United Kingdom .................... 9411636
Jun. 13, 1994 [GB] United Kingdom .................... 9411797

[51] Int. Cl.⁶ ........................ A61K 31/35; C07D 311/68; C07D 311/72

[52] U.S. Cl. .......................... 514/455; 514/456; 514/302; 549/389; 549/399; 546/116

[58] Field of Search ............................ 546/116; 549/389, 549/399; 514/302, 455, 456

[56] References Cited

U.S. PATENT DOCUMENTS

| | | | |
|---|---|---|---|
| 3,789,056 | 1/1974 | Pfirrmann | 260/239.6 |
| 4,571,406 | 2/1986 | Evans | 514/456 |
| 5,021,432 | 6/1991 | Yamanaka | 514/337 |
| 5,624,954 | 4/1997 | Evans | 514/456 |

FOREIGN PATENT DOCUMENTS

| | | |
|---|---|---|
| WO 92/22293 | 12/1992 | WIPO . |
| WO 94/13656 | 6/1994 | WIPO . |
| WO 94/13657 | 6/1994 | WIPO . |

*Primary Examiner*—Evelyn Huang
*Attorney, Agent, or Firm*—Mary E. McCarthy; Charles M. Kinzig; Stephen Venetianer

[57] ABSTRACT

The invention provides certain 5 and/or 8 substituted benzopyran, pyranopyridine or tetrahydroquinaline compounds having $C_4$-amide substituent and processes for making them. The compounds described are useful in treating and/or preventing certain disorders.

16 Claims, No Drawings

C4-AMIDE SUBSTITUTED COMPOUNDS AND THEIR USE AS THERAPEUTIC AGENTS

This application is the national phase of POT/EP95/02,149, filed Jun. 9,1995 issued as WO 95/34,547 on Dec. 21, 1995.

This invention relates to novel compounds, to processes for preparing them, and to their use as therapeutic agents.

European Published Patent Application No. 0126311 discloses substituted benzopyran compounds having blood pressure lowering activity, including 6-acetyl-trans-4-(4-fluorobenzoylamino)- 3,4-dihydro-2,2-dirmethyl-2H- 1-benzopyran-3-ol.

Also EP-A-0 376 524, EP-A-0 205 292, EP-A-0 250 077, EP-A-0 093 535, EP-A-0 150 202, EP-A-0 076 075 and WO/89/05808 (Beecham Group plc) describe certain benzopyran derivatives which possess anti-hypertensive activity.

EP-A-0 350 805 (Biersdorf), EP-A-0 277 611, EP-A-0 277612, EP-A-0 337 179 and EP-A-0 355 565 (Hoechst Aktiengesellschaft); EP-A-0 466 131 (Nissan Chemical Industries Ltd), EP-A-0339562 (Yoshitomi Pharmaceuticals) EP-A-415 065 (E. Merck) EP-A-450415 (Squibb), EP-A-0482934, EP-A-0296975, EPA 571822 (Daiichi Pharm.), JO-2004-791 and WO\89\07103 also describe certain benzopyran derivatives which are believed to possess anti-hypertensive activity.

EP-A-0 430 621 and EP-A-0 385 584 (Beecham Group plc) describe the resolution of certain intermediates useful in the preparation of the compounds described in the above mentioned patent applications.

EP-A-0 139 992 (Beecham Group plc) describes certain benzopyran derivatives which have cis isomerism at position 3 and 4 which compounds are described as possessing anti-hypertensive activity.

PCT/GB92/01045 (SmithKline Beecham plc; unpublished at the priority date), which describes certain fluorobenzoylamino benzopyrans, pyranopyridines and tetrahydronaphthalenes in which the 3 and 4 position substituents are trans to each other. These compounds are described as possessing inter alia anxiolytic and anti-convulsant activity.

It has now been surprisingly found that certain compounds of formula (I) (below) possess anti-convulsant activity, and are therefore believed to be useful in the 30 treatment and/or prevention of epilepsy; the compounds of formula (I) are also believed to have utility in the treatment or prevention of anxiety, mania, depression, disorders associated with a subarachnoid haemorrhage or neural shock, the effects associated with withdrawal from substances of abuse, Parkinson's Disease, psychosis, migraine, cerebral ischaemia, Alzheimer's disease, schizophrenia, OCD (obsessive compulsive disorder), panic disorders and/or agression.

Accordingly, the present invention provides a compound of formula (I) or pharmaceutically acceptable salt thereof:

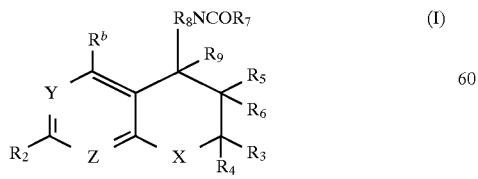

(I)

wherein:
either Y is N and $R_2$ is hydrogen, or Y is C—$R_1$; where:
either one of $R_1$ and $R_2$ is hydrogen and the other is selected from the class of hydrogen, $C_{3-8}$ cycloalkyl, $C_{1-6}$ alkyl optionally interrupted by oxygen or substituted by hydroxy, $C_{1-6}$ alkoxy or substituted aminocarbonyl, $C_{1-6}$ alkylcarbonyl, $C_{1-6}$ alkoxycarbonyl, $C_{1-6}$ alkylcarbonyloxy, $C_{1-6}$ alkoxy, nitro, cyano, halo, trifluoromethyl, $CF_3S$, or a group $CF_3$—A—, where A is —$CF_2$—, —CO—, —$CH_2$—, CH(OH), $SO_2$, SO, $CH_2$—O, or CONH, or a group $CF_2H$—A'—where A' is oxygen, sulphur, SO, $SO_2$, $CF_2$ or CFH; trifluoromethoxy, $C_{1-6}$ alkylsulphinyl, perfluoro $C_{2-6}$ alkylsulphonyl, $C_{1-6}$ alkylsulphonyl, $C_{1-6}$ alkoxysulphinyl, $C_{1-6}$ alkoxysulphonyl, aryl, heteroaryl, arylcarbonyl, heteroarylcarbonyl, phosphono, arylcarbonyloxy, heteroarylcarbonyloxy, arylsulphinyl, heteroarylsulphinyl, arylsulphonyl, heteroarylsulphonyl in which any aromatic moiety is optionally substituted, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulphinyl, aminosulphonyl or aminocarbonyl, any amino moiety being optionally substituted by one or two $C_{1-6}$ alkyl groups, or $C_{1-6}$ alkylsulphinylamino, $C_{1-6}$ alkylsulphonylamino,$C_{1-6}$ alkoxysulphinylamino or $C_{1-6}$ alkoxysulphonylamino, or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is halo, $C_{1-4}$ alkyl, methoxy or amino optionally substituted by one or two $C_{1-6}$ alkyl or by $C_{2-7}$ alkanoyl; or $R_1$ and $R_2$ together are —(CH$_2$)$_4$—; (CH$_2$)$_{X\ CO\ (CH2)}$y where x is 0 to 3 and y is 0 to 3 with the proviso that x+y is at least 2×; or —CH=CH—CH=CH—; or form an optionally substituted triazole or oxadiazole ring, or together form a group CONR$^C$CO where R$^C$ is hydrogen, $C_{1-6}$ alkyl, aralkyl or heteroarylalkyl;
either Z is N only when Y is C—$R_1$ or Z is C—R$^a$ when Y is N or C—$R_1$, wherein R$^a$ is hydrogen, halogen, nitro $C_{1-4}$ alkylcarbonyl, $C_{1-4}$ alkyl; aryl $C_{1-4}$ alkyl, aryl $C_{1-4}$alkenyl, heteroaryl $C_{1-4}$ alkyl or heteroaryl $C_{1-4}$ alkenyl, R$^b$ is hydrogen, halogen, nitro; $C_{1-4}$ alkylcarbonyl or $C_{1-4}$ alkyl with the proviso that R$^a$ and R$^b$ are not simultaneously hydrogen except in the case where one of $R_1$ and $R_2$ is nitro, cyano, or $C_{1-3}$ alkylcarbonyl and the other is halo or $C_{1-4}$ alkyl; and in which any aryl or heteroaryl or alkyl moiety associated with R$^a$ or R$^b$ are optionally substituted; one of $R_3$ and $R_4$ is hydrogen or $C_{1-4}$ alkyl and the other is $C_{1-4}$ alkyl, $CF_3$ or $CH_2X^a$ where X$^a$ is fluoro, chloro, bromo, iodo, $C_{1-4}$ alkoxy, hydroxy, $C_{1-4}$ alkylcarbonyloxy, —S—$C_{1-4}$ alkyl, nitro, amino optionally substituted by one or two $C_{1-4}$ alkyl groups; cyano or $C_{1-4}$ alkoxycarbonyl or $R_3$ and $R_4$ together are $C_{2-5}$ polymethylene optionally substituted by $C_{1-4}$ alkyl;
$R_5$ is $C_{1-6}$ alkylcarbonyloxy, benzoyloxy, ONO$_2$, benzyloxy, phenyloxy or $C_{1-6}$ alkoxy and $R_6$ and $R_9$ are hydrogen or $R_5$ is hydroxy and $R_6$ and $R_9$ are independently hydrogen or $C_{1-2}$ alkyl;
$R_7$ is heteroaryl or phenyl; both of which are optionally substituted one or more times independently with a group or atom selected from chloro, fluoro, bromo, iodo, nitro, amino optionally substituted once or twice by $C_{1-4}$ alkyl, cyano, azido, $C_{1-4}$ alkyl, $C_{1-4}$ alkoxy, trifluoromethoxy, trifluoromethyl; optionally substituted aryloxy or heteroaryloxy;

$C_{1-4}$ alkoxy substituted by one or more halogens (excluding trifluoromethoxy);

amino substituted by $C_{1-4}$ alkanoyl, aroyl aryl phenylsulphonyl or $C_{1-4}$ alkylsulphonyl;

$C_{1-4}$ alkyl substituted by one or more halogens (excluding trifluoromethyl) or alkoxy;

phenylsulphonyl $C_{1-4}$ alkyl sulphonyl, aminosulphonyl in which the amino group is optionally substituted by $C_{1-4}$ alkyl;

$CONH_2$ in which the amino group is optionally substituted by $C_{1-4}$ alkyl;

$R_8$ is hydrogen; $C_{1-6}$ alkyl, $OR_c$ or $NHCOR_{10}$ wherein $R_c$ is hydrogen, $C_{1-6}$ alkyl, formyl, $C_{1-6}$ alkanoyl, aroyl or aryl-$C_{1-6}$ alkyl and $R_{10}$ is hydrogen, $C_{1-6}$ alkyl, $C_{1-6}$ alkoxy, mono or di $C_{1-6}$ alkyl amino, amino, amino-$C_{1-6}$ alkyl, hydroxy-$C_{1-6}$ alkyl, halo-$C_{1-6}$ alkyl, $C_{1-6}$ acyloxy-$C_{1-6}$ alkyl, $C_{1-6}$ alkoxycarbonyl-$C_{1-6}$-alkyl, aryl or heteroaryl;

the $R_8$-N-CO-$R_7$ group being cis or trans to the $R_5$ group;

and X is oxygen or $NR_{10}$ where $R_{10}$ is hydrogen or $C_{1-6}$ alkyl.

All $C_{1-6}$ alkyl or $C_{1-4}$ alkyl or alkyl containing groups in formula (I) are preferably selected from methyl, ethyl, n- and iso -propyl, n -, iso -, sec - and tert-butyl.

Suitable $C_{3-8}$ cycloalkyl groups include cyclopropyl, cyclobutyl, cyclopentyl, cyclohexyl, cycloheptyl and cyclooctyl.

Suitable halo substituents include fluoro, chloro, bromo and iodo.

Aryl whenever mentioned herein includes but is not limited to phenyl and naphthyl.

Heteroaryl whenever mentioned herein includes a 5- or 6- membered monocyclic or 9- or 10- membered bicyclic of which 5- or 6- membered monocyclic heteroaryl is preferred. In addition, 5- or 6-membered monocyclic or 9- or 10-membered bicyclic heteroaryl preferably contains one, two or three heteroatoms which are selected from the class of oxygen, nitrogen and sulphur and which, in the case of there being more than one heteroatom, are the same or different. Examples of 5- or 6-membered monocyclic heteroaryl containing one, two or three heteroatoms which are selected from the class of oxygen, nitrogen and sulphur include furyl, thienyl, pyrryl, oxazolyl, thiazolyl, imidazolyl and thiadiazolyl, and pyridyl, pyridazyl, pyrimidyl, pyrazolyl and triazolyl. Preferred examples of such groups include furanyl, thienyl, pyrryl and pyridyl, in particular 2- and 3-furyl, 2- and 3-pyrryl, 2- and 3-thienyl, and 2-, 3- and 4-pyridyl. Examples of 9- or 10-membered bicyclic heteroaryl containing one, two or three heteroatoms which are selected from the class of oxygen, nitrogen and sulphur include benzofuranyl, benzothienyl, indolyl and indazolyl, quinolyl and isoquinolyl, and quinazolyl. Preferred examples of such groups include 2- and 3-benzofuryl, 2- and 3-benzothienyl, and 2- and 3-indolyl, and 2- and 3-quinolyl.

Suitable examples of groups or atoms for optional substitution especially of aryl heteroaryl and alkyl moieties, especially associated with $R^a$ and $R^b$ include one, two or three substituents independently selected from $C_{1-4}$ alkyl, $C_{1-4}$ alkoxy $C_{1-4}$ alkyl carbonyloxy, $C_{1-4}$ alkyl carbonyl, halo (such as fluoro, chloro, bromo and iodo), hydroxy, nitro, amino optionally substituted once or twice by $C_{1-4}$ alkyl, cyano and $SO_nH$, where n=0 to 2.

Preferably $R_1$ is acetyl.

Preferably $R_2$ is hydrogen, fluorine or methyl.

When Z is $CR^a$, preferably $R^a$ is hydrogen, iodo, bromo, nitro or acetyl.

Preferably $R^6$ is hydrogen or acetyl.

Preferably $R_3$ and $R_4$ are both methyl.

Preferably $R_5$ is hydroxy and $R_6$ and $R_9$ are hydrogen.

It should be appreciated that when $R_7$ is phenyl optionally independently substituted; this includes substitution by 1,2, 3,4 or 5 groups or atoms attached to the phenyl ring. Preferably there are 1 or 2 groups or atoms attached to the phenyl ring. The groups or atoms may be in any position around the phenyl ring. Likewise, it should be appreciated that when $R_7$ is heteroaryl optionally independently substituted; this includes substituents at any vacant positions around the heteroaryl moiety. Preferably there are 1 or 2 groups or atoms around the heteroaryl moiety, most preferably there is one group or atom around the heteroaryl moiety.

Preferably $R_7$ is 2,3-or 4-fluorophenyl, phenyl, 2 or 3-chlorophenyl, 2,3-dichlorophenyl, 2-trifluoromethylphenyl, 2-nitrophenyl, 2-chloro-thiophen-3-yl, 3-chloro-thiophen-2-yl, 2,5dichloro-thiophen-3-yl or 3-chloro-4-fluorophenyl.

Preferably $R_8$ is hydrogen.

Preferably X is oxygen.

It should be appreciated that the compounds of formula (I) may have chiral carbon atoms at positions in addition to positions 3 and 4 and therefore may exist as enantiomers. The present invention extends to each enantiomer and to mixtures thereof including racemates. It should further be appreciated that particular enantiomeric forms are preferred for different utilities, thus for utilities other than sub-arachnoid haemorrhage or neural shock the 3S, 4S or 3R, 4S enantiomers are preferred, however, for sub-arachnoid haemorrhage or neural shock the 3S, 4R enantiomers are preferred.

It should be appreciated that the compound of formula (I) or a pharmaceutically acceptable salt thereof also includes solvates of such compounds, such as for example the hydrate.

The present invention further provides a compound of formula (I), or a pharmaceutically acceptable salt thereof as hereinbefore defined which exists predominantly in the 3S, 4S enantiomeric form.

It should be appreciated that the term "exists predominantly in the 3S, 4S enantiomeric form" means that there is greater than 50% of the 3S, 4S enantiomer present compared to the 3R, 4R enantiomer.

More preferably there is greater than 60% of the 3S, 4S enantiomer present, yet more peferably greater than 70% of the 3S, 4S enantiomer presence, even more preferably greater than 80% of the 3S, 4S enantiomer present and more preferably still greater than 90% of the 3S, 4S enantiomer present. Most preferably there is greater than 95% of the 3S, 4S enantiomer compound to the 3R, 4R enantiomer. The same applies to the 3R, 4S enantiomeric form.

Example of compounds of formula (I) are:

trans-6-Acetyl-4-(3-azidobenzoylamino)-3,4-dihydro-8-iodo-2,2-dimethyl-2H- 1 -benzopyran-3-ol;

trans-6-Acetyl-4-(2-chlorobenzoylamino)-3,4-dihydro-2,2-dimethyl-2H-pyrano[2, 3-b]pyridin-3-ol;

trans-6-Acetyl-4-(2,3-dichlorobenzoylamino)-3 ,4-dihydro-2,2-dimethyl-2H-pyrano[2, 3-b]pyridin-3-ol;

trans-6-Acetyl-4-(4-fluorobenzoylamino)-3,4-dihydro-2,2-dimethyl-8-nitro-2H- 1-benzopyran-3-ol;

trans-8-Acetyl-4-(4-fluorobenzoylamino)-3,4-dihydro-2,2-dimethyl-2H- 1-benzopyran-3-ol;

trans-8-Bromo-4-(3-bromo-4-fluorobenzoylamino)-6-ethyl-3 ,4-dihydro-2,2-dimethyl-2H-1-benzopyran-3-ol;

trans-5-Acetyl-4-(4-fluorobenzoylamino)-3 ,4-dihydro-2,2-dimethyl-2H-1-benzopyran-3-ol;

trans-6-Acetyl-4S-(3-azidobenzoylamino)-3,4-dihydro-8-iodo-2,2-dimethyl-2H-1-benzopyran-3R-ol;
trans-8-Acetyl-4-(2-chlorobenzoylamino)-3,4-dihydro-2,2-dimethyl-2H-1-benzopyran-3-ol;
trans-8-Acetyl-4-(3-chlorobenzoylamino)-3,4-dihydro-2,2-dimethyl-2H-benzopyran-3-ol;
trans 6-Acetyl-4-(4-fluorophenylbenzoylamino)-3,4-dihydro-2,2-dimethyl-8-(2-phenylethyl)-2H-1-benzopyran-3-ol;
trans 6-Acetyl-4-(4-fluorophenylbenzoylamino)-3,4-dihydro-2,2-dimethyl-8-(2-phenylethenyl)-2H-1-benzopyran-3-ol;
(±)-10-bromo-2,2-dimethyl-trans-4-(4-fluorobenzoylamino)-3,4,6,7,8,9-hexahydro-6-oxo-naphthaleno[3,2-b]pyran-3-ol;
trans-3R,4S-6-Acetyl-4-(3-ethoxymethylbenzoylamino)-3-4-dihydro-8-iodo-2.2-dimethylbenxop[b]pyran-3-ol;
trans-3R,4S-6-Acetyl-4-(3-Acetyloxymethylbenzoylamino)-3,4-dihydro-8-iodo-2,2dimethylbenzol[b]pyran-3-ol;
trans-3R,4S-6-Acetyl-3,4-dihydro-4-(3-hydroxymethylbenzoylamino)-8-iodo-2,2-dimethylbenzo[b]pyran-3-ol;
(±)-2,2-dimethyl-trans-4-(3-chloro-4-fluorobenzoylamino-3,4,6,7,8,9-hexahydro-6-oxo-naphthaleno[3,2-b] pyran-3-ol;
trans-6-Acetyl-3,4-dihydro-2,2-dimethyl-4S-(3-chlorobenzoylamino)-8-iodo-2H-benzo[b]pyran-3R-ol;
cis 6-Acetyl-4S-(3-chlorobenzoylamino)-3,4-Dihydro-2,2-dimethyl-8-hydroxymethyl-2H-benzol[b]pyran-3S-ol;
cis 8-Acetoxymethyl-6-acetyl4S-(3-chlorobenzoylamino)-3,4dihydro-2,2-dimethyl-2H-benzo[b]pyran-3S-ol;
trans-6-Acetyl-4-(4-fluorobenzoylamino)-3,4dihydro-2,2,7-trimethyl-2H-1-benzopyran-3-ol and
trans-6-Acetyl-7-fluoro-4-(4-fluorobenzoylamino)-3,4-dihydro-2,2-dimethyl-2H-1-benzopyran-3-ol.

Such compounds, solvates and pharmaceutically acceptable salt thereof are believed to be novel and form a preferred aspect of the present invention.

The administration to the mammal may be by way of oral or parenteral administration.

An amount effective to treat the disorders hereinbefore described depends on the usual factors such as the nature and severity of the disorders being treated and the weight of the mammal. However, a unit dose will normally contain 1 to 1000 mg, suitably 1 to 500 mg, for example an amount in the range of from 2 to 400 mg such as 2, 5, 10, 20, 30, 40, 50, 100, 200, 300 and 400 mg of the active compound. Unit doses will normally be administered once or more than once per day, for example 1, 2, 3, 4, 5 or 6 times a day, more usually 1 to 4 times a day, such that the total daily dose is normally in the range, for a 70 kg adult of 1 to 1000 mg, for example 1 to 500 mg, that is in the range of approximately 0.01 to 15 mg/kg/day, more usually 0.1 to 6 mg/kg/day, for example 1 to 6 mg/kg/day.

It is greatly preferred that the compound of formula (I) is administered in the form of a unit-dose composition, such as a unit dose oral, such as sub-lingual, rectal, topical or parenteral (especially intravenous) composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing the compound and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

The present invention further provides a pharmaceutical composition for use in the treatment and/or prophylaxis of anxiety, mania, depression, disorders associated with a subarachnoid haemorrhage or neural shock, the effects associated with withdrawal from substances of abuse such as cocaine, nicotine, alcohol and benzodiazepines, disorders treatable or preventable with anti-convulsive agents, such as epilepsy; Parkinson's disease, psychosis, migraine, cerebral ischaemia, Alzheimer's disease, schizophrenia, OCD, panic disorders and/or agression which comprises a compound of formula (I) or a pharmaceutically acceptable salt thereof, and a pharmaceutically acceptable carrier.

The present invention also provides a method of treatment and/or prophylaxis of anxiety, mania, depression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy; Parkinson's disease, psychosis, migraine, cerebral ischaemia, Alzheimer's disease, schizophrenia, OCD, panic disorders and/or agression, comprising administering to the sufferer in need thereof an effective or prophylactic amount of a compound of formula (I) pharmaceutically acceptable salt thereof.

In a further aspect the invention provides the use of a compound of formula (I) including or a pharmaceutically acceptable salt thereof, for the manufacture of a medicament for the treatment and/or prophylaxis of anxiety, mania, depression, disorders associated with a subarachnoid haemorrhage or neural shock, the effects associated with withdrawal from substances of abuse such as cocaine, nicotine, alcohol and benzodiazepines, disorders treatable or preventable with anti-convulsive agents, such as epilepsy; Parkinson's disease, psychosis, migraine, cerebral ischaemia, Alzheimer's disease, schizophrenia, OCD, panic disorders and/or agression.

In a further aspect the present invention provides a pharmaceutical composition containing a compound of formula (I) or a pharmaceutically acceptable salt thereof and a pharmaceutically acceptable carrier.

In a further aspect the invention provides the use of a compound of formula (I) a pharmaceutically acceptable salt thereof as a therapeutic agent, in particular for the treatment and/or prophylaxis of anxiety, mania, depression, disorders associated with a sub-arachnoid haemorrhage, neural shock, the effects associated with withdrawal from substances of abuse such as cocaine, nicotine, alcohol and benzodiazepines; disorders treatable or preventable with anti-convulsive agents, such as epilepsy; Parkinson's disease, pychosis, migraine, cerebral ischaemia, Alzheimer's disease, schizophrenia, OCD, panic disorders and/or agression.

Such compositions may be prepared in the manner as hereinbefore described.

Generally, the trans compounds of formula (I) may be prepared according to or analogously to the procedures described in EP-0126311, EP-0376524, EP-205292, EP-0250077, EP-0093535, EP-0150202, EP-0076075, WO/89/05808, EP-0350805, EP-0277611, EP-0277612, EP-0337179, EP-0339562, EP-0355565, EP-A-415 065 (E. Merck), EP-A-450 415 (Squibb) EP-0466131, EP-A-0482934, EP-A-0296975, JO-2004-791 and WO\89\07103.

The cis compounds may be prepared by procedures generally described in or analogous to those described in EP-A-0139992 or from the corresponding trans compounds.

This cis compounds of formula (I) may also be prepared according to the procedures described by G. Burrell et al, Tet. Letters, 31, 3649–3652 (1990) or by the procedures described by U. Quast and E. Villhauer, Eur. J. Pharmacol, Molecular Pharmacology Section 245, 165–171 (1993).

Conversions of $R_5$ hydroxy and $R_8$ respectively may be carried out, using conventional procedures in the art, in particular using the procedures outlined in the aforementioned patents.

It should be appreciated that racemates for formula (I) may be resolved or enantiomerically purified compounds of formula (I) may be prepared using procedures conventional in the art and in particular using the procedures outlined in EP-0430631 and EP-0355584.

It should also be appreciated that it is preferred that the compounds of formula (I) may be prepared in the required enantiomeric form by forming a chirally pure epoxide using catalysts and conditions generally outlined in WO91\14694 or WO 93\17026 and thereafter converting the epoxides to the required compound of formula (I) using procedures outlined herein.

The trans compounds of formula (I) may further be prepared according to the procedures outlined in PCT/GB92/01045 which procedures are incorporated herein by reference or the trans compounds of formula (I) may be prepared according to methods analogous to these described in the one mentioned patents.

The trans compounds of formula (I) in which $R_5$ is hydroxy, $R_6$ is $C_{1-2}$ alkyl and $R_9$ is hydrogen may be prepared according to the procedures outlined in R. Gericke et al. J. Med. Chem. Vol.34, p3074(1991).

The following compounds were prepared by methods analgous to those described in the abovementioned patents and publications.

The following descriptions, examples and pharmacological test results illustrate the present invention:

DESCRIPTION 1 trans-6-Acetyl-4-amino-3,4-dihydro-8-iodo-2,2-dimethyl-2H-1-benzopyran-3-ol

A mixture of 4-hydroxy-3-iodoacetophenone (5.24 g), 40% sodium hydroxide solution (4.8 ml), water (19 ml), xylene (11 ml) and 3-chloro-3-methylbut-1-yne (4.1 g) was heated to 90° C. for 3 hrs. The mixture was cooled and extracted with ether, and the ether extracts were washed with 2N sodium hydroxide solution, water and brine and dried over anhydrous sodium sulphate. The ethereal solution was filtered and evaporated, and the xylene solution that remained was refluxed for 16 hrs. The solution was evaporated and the residue chromatographed on silica gel using 10% ethyl acetate in hexane to give 6-acetyl-8-iodo-2,2-dimethyl-2H-1-benzopyran as a colourless solid (3.07 g), m.p. 102° C.

To a stirred mixture of the benzopyran (2.4 g) in dimethyl sulphoxide (24 ml) and water (0.17 ml) was added NBS (1.56 g) in one portion. The solution was stirred for 2 h, and then poured into water. Extraction via ethyl acetate gave a crude bromohydrin (2 g) which was heated to 100° C. in a solution of 2M ammonia in dry methanol in a sealed steel container for 16hrs. Aqueous work-up gave the aminoalcohol (0.81 g) of description 1, together with unchanged starting material (1.0 g).

EXAMPLE 1 trans-6-Acetyl-4-(3-azidobenzoylamino)-3,4-dihydro-8-iodo-2,2-dimethyl-2H-1-benzopyran-3-ol To a stirred solution of 3-azidobenzoic acid (161 mg) in DMF (5 ml) was added ethyl dimethylaminopropyl carbodimide hydrochloride (211 mg) and 1-hydroxybenzotriazole (149 mg). The mixture was stirred for 0.5 hr, the aminoalcohol of description 1 (361 mg) added, and stirring continued for an additional 4 hr.

The solution was diluted with ethyl acetate and washed with 1M.HCl, saturated sodium bicarbonate solution, water and brine, and dried over anhydrous sodium sulphate. Filtration and evaporation gave a crude product that was chromatographed on silica gel and eluted with 25% ethyl acetate-hexane and recrystallised from ethyl acetate-hexane to give the compound of example 1 (370 mg); mp 156° C.

DESCRIPTION 2 trans-6-Acetyl-4-amino-3,4-dihydro-2.2-dimethyl-2H-pyrano[2, 3-b]pyridin-3-ol

To a solution of 6-bromo-2,2-dimethyl-2H-pyrano[2,3-b]pyridine (1.2 g, prepared as in Synthetic Communs. 18, 1111 (1988)) in dry ether (30 ml) at −78° C. under Argon, was added dropwise a 2.5M solution of n-BuLi in hexanes (2 ml) over 5 min. followed by N,N-dimethylacetamide (0.55 ml). The resulting solution was stirred and allowed to attain room temperature. Saturated ammonium chloride solution (2 ml) was added to the solution. Extraction via ethyl acetate gave a crude solid (0.93 g) which was flash chromatographed on silica gel using ethyl acetate-hexane (3:7) as eluant to give acetylpyranopyridine (0.62 g) as a colourless solid.

The aminoalcohol was prepared from the acetylpyranopyridine in a similar manner to that described in description 1.

EXAMPLE 2 trans-6-Acetyl-4-(2-chlorobenzoylamino)-3,4-dihydro-2,2-dimethyl-2H-pyrano[2,3-b]pyridin-3-ol The aminoalcohol of description 2 was coupled with 2-chlorobenzoic acid in a similar manner to that described in example 1 to give the compound of example 2 which was recrystallised from acetone. m.p. 243°–244° C.

EXAMPLE 3 trans-6-Acetyl-4-(2,3-dichlorobenzoylamino)-3,4-dihydro-2,2-dimethyl-2H-pyrano[2, 3-b]pyridin-3-ol m.p. 257°–258° C.

EXAMPLE 4 trans-6-Acetyl-4-(4-fluorobenzoylamino)-3,4-dihydro-2,2-dimethy-8-nitro-2H-1-benzopyran-3-ol The appropriate aminoalcohol was prepared from 4-hydroxy-3-nitro-acetophenone as in description 1, and coupled with 4-fluorobenzoic acid as in example 1, to give the compound of example 4; m.p. 212° C.

DESCRIPTION 3

8-Acetyl-3,4-epoxy-3,4-dihydro-2,2-dimethyl-2H-1-benzopyran

8-Acetyl-2,2-dimethyl-2H-1-benzopyran was prepared from 2-hydroxy-acetophenone in a similar manner to that described in description 1, except that thermal cyclisation of the intermediate propargyl ether was effected by refluxing in a solution of xylene, DMF and N, N-diethylaniline. Treatment with NBS/H$_2$O and ring closure of the resulting bromohydrin with potassium hydroxide pellets in ether gave the epoxide of description 3.

EXAMPLE 5 trans-8-Acetyl-4-(4-fluorobenzoylamino)-3,4-dihydro-2,2-dimethyl-2H-1-benzopyran-3-ol 4-Fluorobenzamide (0.77 g) was added to a stirred solution of the epoxide of description 3 (0.60 g) in t-butanol (18 ml). Potassium t-butoxide was added portionwise to the above solution and stirred for 3 hrs at room temperature under Argon. The solution was stirred for an additional 3 hrs at 45° C., cooled, and poured into saturated aqueous ammonium chloride and extracted with ethyl acetate. The organic phase was washed with water and brine and dried over anhydrous sodium sulphate. Filtration and evaporation and chromatography on silica gel, gradient eluting with pentane to 60% ethyl-pentane gave a yellow solid which was recrystallised from ethyl acetate to give the compound of example 5 as lemon-white crystals (0.15 g) of m.p. 263°–264° C.

EXAMPLE 6 trans-8-Bromo-4-(3-bromo-4-fluorobenzoylamino)-6-ethyl-3,4-dihydro-2,2-dimethyl-2H-1-benzopyran-3-ol trans-4-(3-Bromo-4-fluorobenzylamino)-6-ethyl-3,4-dihydro-2,2-dimethyl-2H-1-benzopyran-3-ol (800 mg) and mercuric acetate (701 mg) were heated in glacial acetic acid (10 ml) to 100° C. A solution of bromine (0.113 ml) in glacial acetic acid (5 ml) was added to the heated solution during 15 mins, and the reaction mixture heated for a further 1.5 hrs. The solution was cooled and evaporated and the residue partitioned between dichloromethane and water. The organic layer was washed with brine and dried over anhydrous magnesium sulphate. Filtration and evaporation and radial chromatography (chromatotron, gradient elution 10% dichloromethane—50% dichloromethane in hexane) gave the compound of example 6 (110 mg) as a pale solid of m.p. 70° C.

DESCRIPTION 4

5-Acetyl-3,4-epoxy-3,4-dihydro-2,2-dimethyl-2H-1-benzopyran

3-Hydroxyacetophenone (25 g), sodium hydroxide pellets (11.0 g), 40% benzyltrimethylammonium hydroxide in methanol (38.7 g), and 3-methyl-3-chorobut-1-yne (56.4 g) were stirred in water (200 ml) and dichloromethane (200 ml) for 7 days at room temperature. The layers were separated and the organic phase evaporated. The aqueous layer was extracted with ether and this organic extract combined with the residue from the evaporation of the dichloromethane phase, and washed with dil sodium hydroxide solution. The ether solution was dried over anhydrous magnesium sulphate, filtered and evaporated to leave a residue (25 g).

The crude propargyl ether (25 g) was refluxed in o-dichlorobenzene (60 ml) for 1.5 hrs. Evaporation and dry flash chromatography (3 times) on silica gel using dichloromethane-hexane as eluant gave the 5-acetylbenzopyran (2.8 g). Treatment of this acetyl compound (2.356 g) with NBS (2.314 g) and water (0.208 ml) in DMSO (30 ml), followed by addition to water and extraction via ethyl acetate gave the bromohydrin (2.0 g). This bromohydrin (2.0 g) was stirred with potassium hydroxide pellets (1.82 g) in ether (150 ml) at room temperature under Argon for 3 days. Filtration and evaporation gave the epoxide of description 4 (1.4 g).

EXAMPLE 7 trans-5-Acetyl-4-(4-fluorobenzoylamino)-3,4-dihydro-2,2-dimethyl-2H-1-benzopyran-3-ol To the epoxide of description 4 (600 mg), dissolved in t-butanol (100 ml), was added 4-fluorobenzamide (956 mg), followed by potassium t-butoxide (771 mg). The reaction mixture was heated at 40° C. for 4 days. The mixture was cooled and evaporated, and the residue taken up into ethyl acetate. The organic solution was washed with water, brine and dried under anhydrous magnesium sulphate. Filtration and evaporation and radial chromatography (cromatotron, using dichloromethane (2→20%) in hexane as eluent) gave a crude product that was recrystallised from acetone-hexane (40 mg) with a m.p. 175° C.

EXAMPLE 8 trans-6-Acetyl-4S-(3-azidobenzoylamino)-3,4-dihydro-8-iodo-2,2-dimethyl-2H-1-benzopyran-3R-ol The compound was prepared by epoxidising the chromene of description 1 with the appropriate Jacobsen catalyst, recrystallisation from ethyl acetate hexane gave 6-acetyl-3R,4R-epoxy 3,4-dihydro-8-iodo-2,2-dimethyl-2H-1-benzopyran. Treatment with aqueous amonia at approximately 60° C. and work up and comply with 3-azidobenzoic acid as in example 1 gave the compound of example 8. HPLC on chiral cel OD using ethanol 4% hexane showed enantiomeric purity to be greater than 99.5%

EXAMPLE 9
trans-8-Acetyl-4-(2-chlorobenzoylamino)-3,4-dihydro-2,2-dimethyl-2H-1-benzopyran-3-ol.
m.p. 165°–170° C.

EXAMPLE 10
trans-8-Acetyl-4-(3-chlorobenzoylamino)-3,4-dihydro-2,2-dimethyl-2H-benzopyran-3-ol. m.p. 182°–183° C.

DESCRIPTION 6
Trans-6-Acetyl-4-amino-3,4-dihydro-2,2-dimethyl-8-(2-phenylethenyl)-2H-1-benzopyran-3-ol

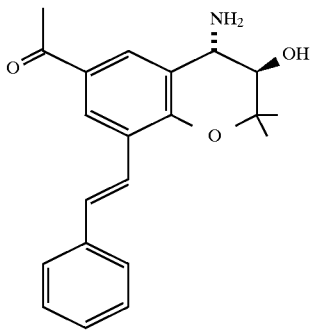

A solution of the aminoalcohol of description 1 (250 mg), styrene (88 mg), triethylamine (700 mg), tri-o-toluene phosphine (22 mg) and palladium (II) acetate (8 mg) in anhydrous acetonitrile (3 ml) under argon was heated at 80° C. for 20 h. The reaction mixture was allowed to cool to room temperature and evaporated to dryness. Silica gel chromatography, eluting with ethanol (5–10%) in ethyl acetate gave the desired product as a solid (150 mg).

DESCRIPTION 7
Trans-6-Acetyl-4-amino-3,4-dihydro-2,2-dimethyl-8-(2-phenylethyl)-benzo-2H-1-pyran-3-ol

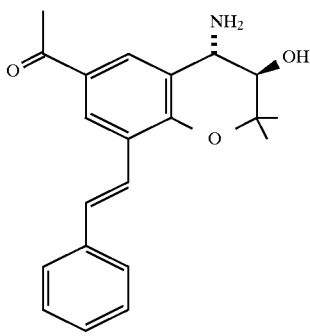

A solution of description 6 (150 mg) and 10% palladium on carbon (10 mg) in ethanol (5 ml) was allow to stir under hydrogen at atmospheric pressure and room temperature for 36 h. The reaction mixture was filtered through a pad of celite and the filtrate evaporated to give crude mixture of desired product and starting material (150 mg).

EXAMPLE 11
Trans 6-Acetyl-4-(4-fluorophenylbenzoylamino)-3,4-dihydro-2,2-dimethyl-8-(2-phenylethyl)-2H-1-benzopyran-3-ol A solution of the mixture of description 7 (150 mg), 4-fluorobenzoyl chloride (70 mg) and diisopropyl ethylamine (57 mg) in dichloromethane (10 ml) was allowed to stir at room temperature for 3 h. The resulting mixture was purified by silica gel chromatography, eluting with ethyl acetate (30%) in hexanes to furnish example 11 (30 mg) mp 197°–198° C.

EXAMPLE 12
Trans 6-Acetyl-4-(4-fluorophenylbenzoylamino)-3,4-dihydro-2,2-dimethyl-8-(2-phenylethenyl)-2H-1-benzopyran-3-ol This example (75 mg) was obtained from the mixture obtained in example 11 with mp 239° C.

DESCRIPTION 8
6-Hydroxy-1-tetralone

A solution of 6-methoxy-1-tetralone (6.0 g, 0.034 moles) in 48% aqueous hydrobromic acid (80 cm$^3$) was refluxed for 2.5 h. The clear orange solution was then cooled to ice temp. and the resulting preicpitate was filtered off under suction, washed with cold water, and dried to afford the title compound as a pale orange solid (5.16 g, 93%), $\delta_H$[250 MHz: (CD$_3$)$_2$SO] 1.99 (2H, m), 2.47 (2H, t), 2.82 (2H, t), 6.64 (1H, d), 6.71 (1H, dd), 7.73 (1H, d) and 10.31 (1H, broad s, OH).

DESCRIPTION 9
6-(methoxyethoxymethoxy)-1-tetralone

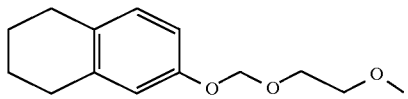

A solution of the phenol (description 8) (2.13 g, 0.0132 moles) in dry DMF (18 cm$^3$) was added dropwise to a suspension of sodium hydride (80% dispersion in oil, 0.435 g, 0.0145 moles) in dry DMF (14 cm$^3$) cooled to ice temp. under argon. After 10 min a solution of 2-methoxyethoxymethyl chloride (1.64 g, 0.0132 moles) was added dropwise. The mixture was stirred at room temp. for 3 h, poured onto water and extracted twice with ethyl acetate. The organic extracts were combined and washed (brine), dried and concentrated to afford the title compound as an orange oil 3.2 g, 97%), $\delta_H$ (250 MHz: CDCl$_3$) 2.12 (2H, m), 2.62 (2H, t), 2.93 (2H, t), 3.39 (3H, s, OCH$_3$), 3.56 (2H, m), 3.82 (2H, m), 5.32 (2H, s, OCH$_2$O), 6.89 (1H, d), 6.96 (1H, dd) and 8.01 (1H, d).

DESCRIPTION 10
5-Bromo-6-(methoxyethoxymethoxy)-1-tetralone

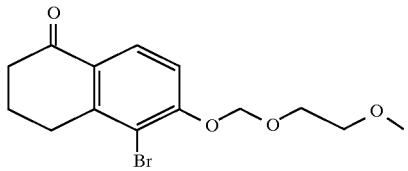

A solution of potassium bromide (10.95 g, 0.092 moles) and sodium acetate (8.15 g, 0.099 moles) in water (33 cm$^3$) was added to a solution of the protected phenol (description 9) (4.62 g, 0.0185 moles) in glacial acetic acid (50 cm$^3$). A solution of bromine (3.14 g, 0.0197 moles) in glacial acetic acid (20 cm$^3$) was added dropwise over 10 mins at room temp. The mixture was heated to 50° C. for 3.5 h and then stirred at room temp. overnight. The yellow solution was concentrated and the residue taken up in ethyl acetate and washed (aqueous sodium bicarbonate, then brine), dried and evaporated. Chromatography on silica gel, elution with ethyl acetate-pentane gradient afforded the title compound (3.18 g, 52%), $\delta_H$ (250 MHz; CDCl$_3$) 2.15 (2H, m), 2.61 (2H, t), 3.03 (2H, t), 3.38 (3H, s, OCH$_3$), 3.55 (2H, m), 3.86 (2H, m), 5.42 (2H, s, OCH$_2$), 7.16 (1H, d) and 8.04 (1H, d).

DESCRIPTION 11
5-Bromo-6-hydroxy-1-tetralone

Trifuloroacetic acid (4 cm$^3$) was added to a stirring solution of the protected phenol (description 10) (3.40 g, 0.0103 moles) in dichloromethane (40 cm$^3$) cooled to ice temp. Stirred for 0.5 h at 0° C. and then for 3 h at room temp. The mixture was neutralised on aqueous sodium bicarbonate and separated. The aqueous layer was extracted with ethyl acetate. The organic layers were each washed (separately) with brine, then combined and dried. Concentration afforded the title compound as a cream-coloured solid (2.5 g, 100%), $\delta_H$ (250 MHz; (CD$_3$)$_2$SO] 2.01 (2H, m), 2.50 (2H, t, overlapped by (CD$_3$)$_2$SO signal), 2.94 (2H, t), 6.94 (1H, d), 7.79 (1H, d), and 11.22 (1H, s, AROH).

DESCRIPTION 12
10-Bromo-2,2-dimethyl-6-oxo-6,7,8,9-tetrahydronaphthaleno[3,2-b]pyrene

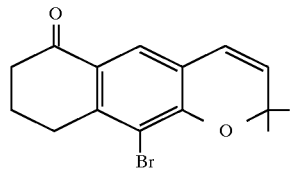

A solution of sodium hydroxide (1.2 g, 0.03 moles) in water (24 cm$^3$) was added to a stirring suspension of the phenol (description 1) (2.5 g, 0.0104 moles) and 3-chloro-3-methyl-but-1-yne (2.4 g, 0.0234 moles) in xylene (24 cm$^3$), The mixture was heated to 70° C. for 2.3 h, cooled, poured onto aqueous ammonium chloride and extracted twice with ethyl acetate. The extracts were washed (brine), dried and concentrated. Re-dissolved in N,N-dimethylformamide (20 cm$^3$) and heated to 140° C. for 20 h. Poured onto water and extracted with diethyl ether. Washed (brine), dried and concentrated. Chromatography on silica ge. elution with ether-pentane gradient gave the title compound as a yellow solid (0.40 g, 13%). $\delta_H$ (250 MHz; CDCl$_3$) 1.51 (6H, s), 2.13 (2H, m), 2.59 (2H, t), 2.98 (2H, t), 5.69 (1H, d), 6.33 (1H, d) and 7.70 (1H, s).

DESCRIPTION 13
(±)-trans-3,3,10-dibromo-2,2-dimethyl-3,4,6,7,8,9-hexahydro-6-oxo-naphthaleno[3,2-b]pyran-4-ol, 6

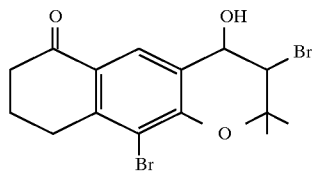

The chromene (description 12) (0.27 g, 0.88 mmol) was stirred in dimethylsulphoxide (8 cm$^3$) until dissolution was complete, and then water (4 drops) was added followed by N-Bromosuccinimide (0.22 g, 1.23 mmol). The mixture was kept at room temp. for 0.75 h and then partitioned between water and ethyl acetate. The organic phase was washed (brine), dried and concentrated to afford the title compound as a beige solid (0.34 g, 96%), $\delta_H$ (250 MHz; CDCl$_3$) 1.45 (3H, s), 1.71 (3H, s), 2.12 (2H, m), 2.60 (2H, t), 2.99 (2H, t), 4.14 (1H, d) 4.94 (1H, d) and 8.24 (1H, s).

DESCRIPTION 14
(±)-10-Bromo-3,4-epoxy-2,2-dimethyl-3,4,6,7,8,9-hexahydro-6-oxo-naphthaleno[3,2-b]pyran (±cis)

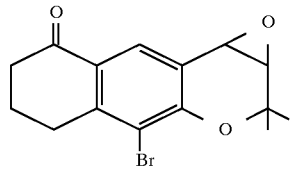

A solution of sodium hydroxide (0.34 g, 8.5 mmol) in water (5 cm$^3$) was added to a stirring solution of bromohydrin (description 13) (0.34 g, 0.84 mmol) in 1,4-dioxane (25 cm$^3$). The mixture was stirred at room temp. for 4 h and then poured onto aqueous ammonium chloride solution. Extracted twice with ethyl acetate. The extracts were combined, washed (brine), dried and then concentrated to give the title compound as a pale brown oil (0.272 g, quant.) $\delta_H$ (250 MHz; CDCl$_3$) 1.31 (3H, s), 1.68 (3H, s), 2.13 (2H, m), 2.61 (2H, m), 3.01 (2H, m), 3.53 (1H, d), 3.97 (1H, d) and 8.10 (1H, s).

DESCRIPTION 13
(±)-trans-4-amino-10-bromo-2,2-dimethyl-3,4,6,7,8,9-hexahydro-6-oxo-naphthaleno[3,2-b]pyran-3-ol

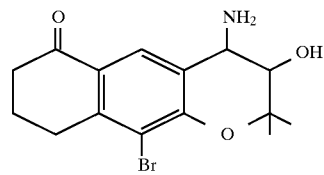

35% aqueous ammonia (12 cm$^3$) was added to a stirring solution of epoxide (description 14)(0.27 g, 0.79 mmol) in ethanol (16 cm$^3$). The mixture was stirred at room temp. for four days and then concnetrated. Re-dissolved in 10% methanol-ethyl acetate (50 cm$^3$) and dried over magnesium sulphate. Evaporation afforded the title compound (0.26 g, 91%). $\delta_H$ (250 MHz; (CD$_3$)$_2$SO] 1.21 (3H, s), 1.43 (3H, s), 2.03 (2H, m), 2.52 (2H, m, overlapped by (CH$_3$)$_2$SO signal), 2.89 (2H, t), 3.21 (1H, d, partially obscured by H$_2$) signal), 3.58 (1H, d), 5.61 (1H, broad s) and 8.20 (1H, s).

EXAMPLE 13
(±)-10-Bromo-2,2-dimethyl-trans-4-(4-fluorobenzoylamino)-3,4,6,7,8,9-hexahydro-6-oxo-naphthaleno[3,2-b]pyran-3-ol

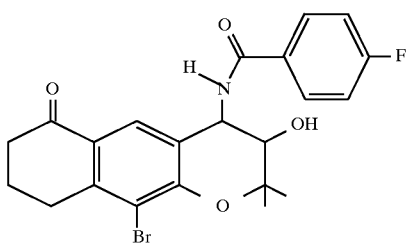

A solution of 4-fluorobenzoyl chloride (97 mg, 0.61 mmol) in dichloromethane (4 cm³) was added dropwise to a stirring solution of amino-alcohol (description 15) (0.20 g, 0.59 mmol) and triethylamine (62 mg, 0.61 mmol) in dichloromethane (16 cm³) cooled to ice temp. The mixture was stirred at room temp. under argon atmosphere overnight. Poured onto aqueous sodium bicarbonate solution and spearated. The aqueous was extracted with chloroform. The organic phases were combeind, washed (brine) dried and concentrated. Chromatography on silica gel, elution with 2% methanol-dichloromethane afforded the title compound as a yellow powder (0.21 g, 77%), (Found: C, 57.18; H, 4.57; N, 3.09. $C_{22}H_{21}BrFNO_4$ requires C, 57.16; H, 4.58; N, 3.03), $\delta_H$ (250 MHz; CDCl₃) 1.23 (3H, s), 1.51 (3H, s), 2.02 (2H, m), 2.49 (2H, m, overlapped by $(CH_3)_2SO$ signal), 2.92 (2H, m), 3.82 (1H, q), 5.08 (1H, broad t), 5.82 (1H, d) 7.37 (2H, m), 7.70 (1H, s), 799 (2H, m) and 8.82 (1H, d).

DESCRIPTION 16
3-Bromophenylmethyl ethyl ether

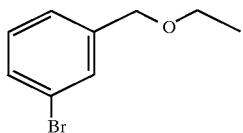

To a solution of 3-Bromobenzylalcohol (4.5 g) in dry dichloromethane (30 ml) at −40° C., was added dropwise, 2,6-lutidine (3 mL), followed by triflate anhydride (4.1 mL). The resulting solution was allowed to stir from −40° C. to 0° C. during 4 hours. The solution was evaporated to dryness in vacuo and then mixed with absolute ethanol (30 mL) and otassium carbonate 96.9 g) for 16 hours at room temperature. Ethanol was removed in vacuo and the residue was purified by aqueous extractive work-up using diethyl ether folowed by silica gel chromatography (20% ethyl acetate/hexane) to give product as a folourless oil (4.62 g, 88%).

DESCRIPTION 17
3-Ethoxymethylbenzoic acid

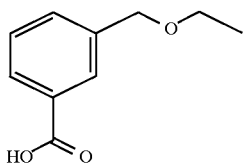

To a solution of description 16 (4.62 g) in dry tetrahydrofuran (40 mL) under argon at −70° C., was added dropwise, a 1.6M solution of butyllithium in hexane (17 mL). The resulting solution was then allowed to stir at −20° for 40 minutes before quenched by the addition of carbon dioxide solids. The mixture was allowed to warm up to room temperature and the tetrahydrofuran removed in vacuo. The oily residue was taken up in diethyl ether and extracted with water twice. The combined aqueous solution was acidified to pH 1 with 5M hydrochloric acid, extracted with ethyl acetate twice. The combined ethyl acetate layer was washed with water and brine and dried over anhydrous sodium sulphate powder. The solution was evaporated to dryness in vacuo to afford product as an oil which solidified ons tanding (2.31 g).

EXAMPLE 14
Trans-3R,4S-6-Acetyl-4-(3-ethoxymethylbenzoylamino)-3-4-dihydro-8-iodo-2,2-dimethylbensop[b]pyran-3-ol

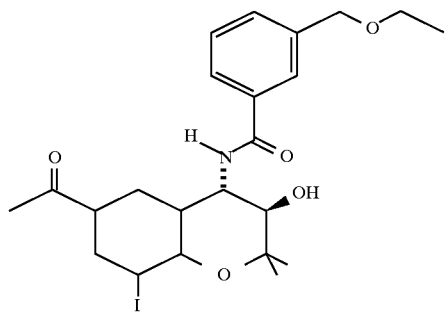

To a stirred solution of description 17 (0.22 g) in dry dimethylformamide (5 mL), was added dimethlaminopropyl ethylcarbodiimide hydrochloride (0.21 g) and 1-hydroxybenzotriazole (0.15 g). 3R,4S-6-acetyl-4-amino-3,4-dihydro-3-hydroxy-8-iodo-2,2-dimethylbenso[b]pyran (0.36 g) was added 30 minutes later. The resulting mixture was allowed to stir for 16 hours before poured into water and extracted with ethyl acetate. The organic layer was washed with brine and dried over anhydrous sodium sulphate powder. Evaporated of the solvent gave product residue which was purified by silica gel chromatography 930% ethyl acetate/hexane), followed by recrystallisation from ethyl acetate/hexane to afford a colourless solid (0.55 g) mp. 162° C.

DESCRIPTION 17
3-acetyloxymethylbenzoic acid

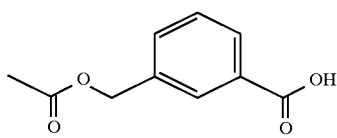

To a solution of 3-acetyloxymethylbenzyl alchohol (prepared by acetylation of 1,3-dihydroxymethylbenzene) (2.92 g) in pyridine (25 mL), was added a solution of tetra-n-butylammonium permanganate (12 g) in pyridine (25 mL) dropwise. The mixture was allowed to stir at room temperature for 3 hours and then poured into cold 2M hydrochloric acid (200 mL) containing sodium metabusulfite (10 g). The mixture was extracted with diethyl ether (150 mL×3). The combined ether solution was washed with 1M hydrochloric acid, followed by saturated sodium bicarbonate solution (150 mL×2). The combined alkaline solution was acidified by addition of hydrochloric acid and then extracted with diethyl ether (200 mL×2). The combined ether layer was washed with water and then brine, dried over anhydrous sodium sulphate powder. This ether solution was concentrated down to 30 mL to give some precipitate which was removed by filtration. The remaining filtrate was evaporated to dryness to afford product as a colourless solid (1.7 g).

EXAMPLE 15

Trans-3R,4S-6-Acetyl-4-(3-Acetyloxymethylbenzoylamino)-3,4-dihydro-8-iodo-2,2-dimethylbenzol[b]pyran-3-ol

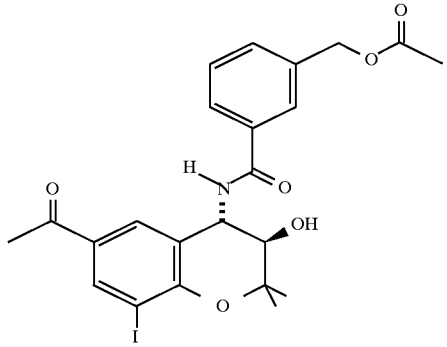

To a stirred solution of description 18 (1.03 g) in dry dimethylformamide (5 mL), was added dimethylaminopropyl ethylcarbodiimide hydrochloride (1.02 g) and 1-hydroxybenzotriazole (0.72 g). 3R,4S-6-acetyl-4 amino-3,4-dihydro-3-hydroxy-8-iodo-2,2-dimethylbenzol[b]pyran (1.74 g) was added 15 minutes later. The resulting mixture was allowed to stir for 3 hours before poured into water and extracted with ethyl acetate. The organic layer was washed with brine and dried over anhydrous sodium sulphate powder. Evaporated of the solvent gave product residue which was purified by silica gel chromatography (50% ethyl acetate/hexane), followed by recrystallisation from ethyl acetate/hexane to afford a colourless solid (1.85 g) mp. 167° C.

EXAMPLE 16

Trans-3R,4S-6-Acetyl-3,4-dihydro-4-(3-hydroxymethylbenzoylamino)-8-iodo-2,2-dimethylbenzo[b]pyran-3-ol

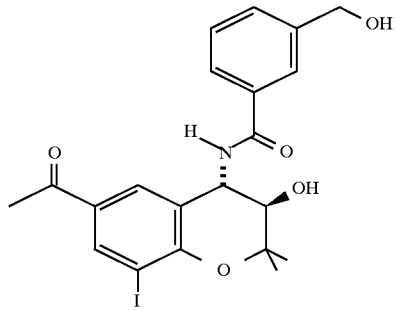

To solution of example 15 (0.82 g) in p-dioxane, was added a 1M solution of lithium hydroxide in water (2 mL). The solution was allowed to stir for 2.5 hours before poured into water (150 mL). The precipitate was collected by filtration, air-dried and recrystallised from hot ethyl acetate to afford product as colourless solid crystalline (0.72 g) mp. 222° C.

DESCRIPTION 19

(±)-trans-4-amino-2,2-dimethyl-3,4,6,7,8,9-hexahydro-6-oxo-naphthaleno[3,2-b]pyran-3-ol

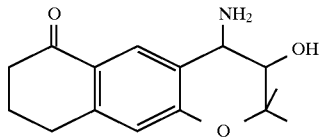

A solution of description 15 (1.32 g, 3.88 mmol) in ethanol (50 cm$^3$) was hydrogenated over 5% Palladium on charcoal (0.30 g) under 1 atmosphere of hydrogen and at room temperature for a total of 60 hours, refreshing the catalyst as necessary. The mixture was filtered through kieselguhr, washing the residues with ethanol. The filtrate was then evaporated to afford the title compound as a yellow solid (0.84 g, 83%). $\delta_H$[250MHz, (CD$_3$)$_2$SO] 1.13(3H,s), 1.42(3H,s) 2.00(2H, m), 2.54 (2H, m, partially obscured by (CH$_3$)$_2$SO signal), 2.88(2H,t), 3.59(1H,q), 4.22(1H,d), 6.28 (1H,d), 6.79(1H,s), 8.20(1h,S) AND 8.45 (2H, broad s, NH$_2$).

EXAMPLE 17

(±)-2,2 -dimethyl-trans-4-(3-chloro-4-fluorobenzoylamino-3,4,6,7,8,9-hexahydro-6-oxo-naphthaleno[3,2-b] pyran-3-ol

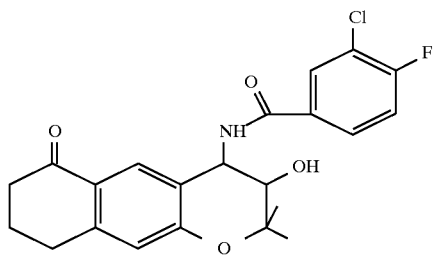

1-ethyl-3-(3-dimethylaminopropyl)carbodamide hydrochloride (0.65 g, 3.39 mmol) was added to a stirring solution of 3-chloro-4-fluorobenzoic acid (0.59 g, 3.38 mmol) and 1-hydroxybenzotriazole hydrate (0.45 g, 3.34 mmol) in dry N,N-dimethylformamide (DMF) (20 cm$^3$). After stirring at room temperature under an atmosphere of argon for 0.5 h, triethylamine (0.34 g, 3.36 mmol) was added. A solution of the amino-alcohol, (description 19), in dry DMF (25 cm$^3$) was then added and stirring was combined for a further 2.5 h. The mixture was poured onto brine and extracted twice with ethyl acetate. The organic extracts were combined and washed (water, brine), dried and concentrated, chromatography on silica gel, elution with ethyl acetate-pentane gradient afforded the title compound, which was recrystallised from an ethyl acetate-hexane mixture to give a yellow powder (0.52 g, 39%). $\delta_H$(250 MHz; CDCl$_3$) 1.30 (3H,S), 1.53(3H,S), 1.98(2H,m), 2.20(1H,m), 2.48(1H,m), 2.78(2H, m), 3.75(1H,dd), 4.32(1H,d), 5.22(IH,t), 6.66(1H,S), 7.13 (1H,S), 7.45(1H,d), 7.82(1H,m), 7.88(1H,S) and 8.07(1H, dd).

EXAMPLE 18 trans-6-Acetyl-3,4-dihydro-2,2-dimethyl-4S-(3-chlorobenzoylamino)-8-iodo-2H-benzo[b]pyran-3R-ol

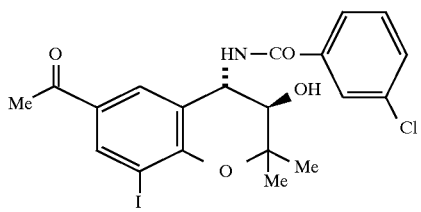

A solution of the amino alcohol (description 1) (500 mg; 1.38 mmol) in dry dichloromethane (15 ml) containing dry triethylamine (0.4 ml) was treated with 3-chlorobenzoyl chloride (314 mg; 1.79 mmol). Recrystallization of the product from ethyl acetate-n-hexane gave the title compound as white crystals (475 mg; 69%).

m.p. 171°–30° C. $^m/z$: 499 (M$^+$; 1%), 466 (15), 329 (10), 139 (100), 111(77)

DESCRIPTION 20
cis 8-Acetyl-2-(3-chlorophenyl )-3a,9b-dihydro-4,4-dimethyl-6-iodo-4H-1-benzol[b]pyran[4,3-d]oxazole

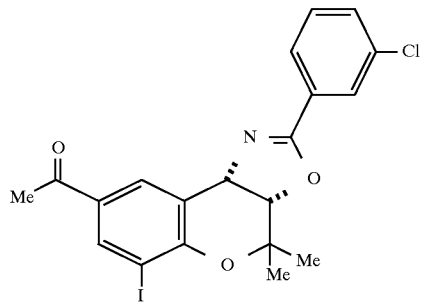

A solution of the benzamide (example 18) (2.2 g; 4.41 mmol) in dry dichloromethane (50 ml) was treated with DAST (0.76 ml; 5.73 mmol) and the mixture kept at room temperature for 1 day. Evaporation in vacuo gave a pale gum which was chromatographed on Kieselgel 60 in 20% ethyl acetate/n-hexane. Combination of appropriate fractions gave the title compound as a colourless gum (1.6 g; 75%).

v max: 2982, 2916, 1682, 1644, 1596, 1573, 1267 and 715 cm$^{-1}$

Found M$^+$ 482.990976 calc. for C$_{20}$H$_{17}$NO$_3$I$^{37}$Cl 482.993903

M$^+$ 480.995986 calc. for C$_{20}$H$_{17}$NO$_3$I$^{35}$Cl 480.994173

DESCRIPTION 21
cis 8-Acetyl-2-(3-chlorophenyl)-3a,9b-dihydro-4,4-dimethyl-6-hydroxymethyl-4H-benzol[b]pyrano[4,3-d]oxazole

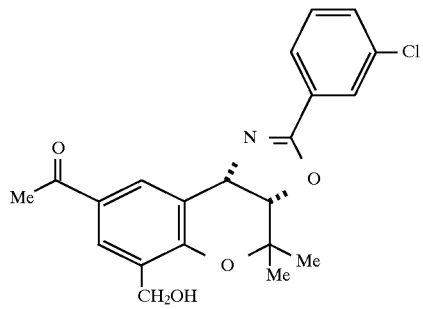

A solution of the 8-iodo-oxazoline (description 20) (1.00 g; 2.07 mmol) in dry 1,3-dixoan (8 ml) was treated with tributyltinmethanol (766 mg; 2.39 mmol; prepared using method W. Clark Still et al, J. Am. Chem. Soc, 1978 100 1481) and tetrakis (triphenylphosphine) palladium (200 mg) under an argon atmosphere. The mixture was heated at 80° C. with stirring under argon for 1 day and then evaporated to dryness in vacuo. The black residue was dissolved in acetonitrile (30 ml) and washed with n-hexane (3×20 ml); evaporation of the acetonitrile layer gave a light tan gum (1.1 g). Chromatography on Kieselgel 60 in 15%–30% ethyl acetate/n-hexane gave pure title compound as a pale yellow gum (560 mg; 70%).

$^1$H NMR in CDCl$_3$ δ: 1.38 and 1.61 (2×3H, S), 2.50 (3H,s) 2.11 (1H, t, collapses with D$_2$O), 4.70 (2H, d, collapses to s with D$_2$O), 4.80 and 5.38 (2H, ABq), 7.33 (1H, t), 7.45 (1H, dd), 7.77–8.00 (3H, m) and 8.09 (1H,d).

EXAMPLE 19
cis 6-Acetyl-4S-(3-chlorobenzoylamino)-3,4-Dihydro-2,2-dimethyl-8-hydroxymethyl-2H-benzol[b]pyran-3S-ol

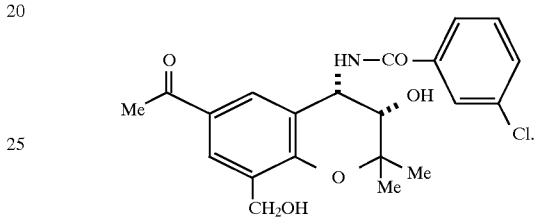

The foregoing oxazoline (description 21) (540 mg; 1.45 mmol) in 1,4-dioxan (15 ml), water (5 ml) and 5n H$_2$SO$_4$ (2 ml) was kept at 25° C. for 2 days. An excess of solid NaHCO$_3$ was added and the suspension stirred for 2 h. Evaporation in vacuo followed by partition between ethyl acetate and water gave the product from the organic phase. Recrystaliisation from dichloromethane/hexane/methanol afforded the title compound was white crystals (355 mg; 88%) m.p. 217°–9° C.

v max: 3332, 2900, 1668, 1650, 1604, 1520 and 746 cm$^{-1}$

EXAMPLE 20
cis 8-Acetoxymethyl-6-acetyl4S-(3-chlorobenzoylamino)-3,4-dihydro-2,2-dimethyl-2H-benzo[b]pyran-3S-ol

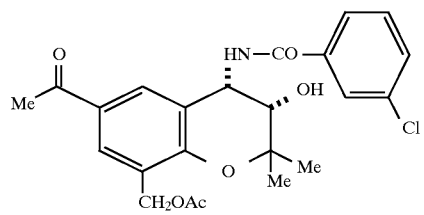

A solution of alcohol (example 19) (120 mg; 0.3 mmol) in dry THF (6 ml) containing acetic anhydride (45 mg; 0.44 mmol) and dry triethylamine (0.1 ml) was heated at 80° under argon for 20 h. Evaporation in vacuo gave a pale yellow gum which was chromatographed on Kieselgel 60 in 15–30% ethyl acetate/n-hexane. Combination of appropriate fractions gave the title compound as white crystals (57 mg; 43%).

m.p. 172°–173.5° C. (from ethyl acetate/pentane)

$^m/z$: CI$^+$463 (MNH$_4$+, 100%), 446 (MH$^+$, 6%).

EXAMPLE 21
Trans-6-Acetyl-4-(4-fluorobenzoylamino-3,4-dihydro-2,2,7-trimethyl-2H-1-benzopyran-3-ol Crystals of m.p. 162°–163° C. from ethyl acetate-petrol.

¹H NMR (250 MHz) CDCl₃ δ:1.32 (3H, s), 2.47 (6H, s), 3.74 (1H,dd), 4.29 (1H, d), 5.26 (1H, t), 6.58 (1H, s), 6.70 (1H, s), 7.16 (2H, t), 7.68 (1H, s), 7.87 (2H,m).

EXAMPLE 22 trans-6-Acetyl-7-fluoro-4-(4-fluorobenzoylamino)-3,4dihydro-2,2-dimethyl-2H-1-benzopyran-3-ol Crystals of m.p. 200°–203° C. from ethyl acetate-hexane.

¹H NMR (250 MHz) CDCl₃ δ: 1.32 (3H, s), 1.52 (3H, s), 2.55 (3H, d), 3.78 (1H,dd), 4.75 (1H, d), 5.21 (1H, t), 6.58 (1H, d), 7.11 (2H, t), 7.76 (1H, d, NH), 7.85 (1H, d), 7.96 (2H, m).

PHARMACOLOGICAL DATA

1. Rat Social Interaction Test

The compounds of formula (I) or pharmaceutically acceptable salts thereof may be tested for therapeutic utility using the procedure outlined as follows:

Potential anxiolytic properties are evaluated using the rat social interaction procedure based on that originally described by File (1980, J. Neurosci. Methods, 2, 219–238). In this model anxiolytic agents selectively increase social interaction independently of any effect on locomotor activity.

Method

Male Sprague—Dawley rats (Charles River. U.K., 250–300 g) are singly housed for 3 days prior to testing. On the test day, the animals are then randomly assigned to groups of 8–16 and dosed orally at a dose volume of 1 ml/kg with various doses of compound (1–300 mg/kg) or vehicle. At 60 min post dose the rats are placed with a weight- and treatment-matched pair male (encountered for the first time) in the social interaction box under high - light, unfamiliar conditions. The box is made of white perspex 54×37×26 cm with a transparent perspex front side. The floor is divided into 24 equal squares and is brightly lit (115 lux). Time spent (secs) in active social interaction (sniffing, grooming, following, mounting, climbing over or under, boxing, biting) is scored "blind" by remote monitoring as is the number of squares crossed (as an index of locomotion).

The mean and standard error for time spent in social interaction and number of squares crossed are then calculated for each particular treatment group and drug-induced changes are expressed as a percentage increase or decrease from control values. Statistical comparisons are made between vehicle- and drug-treated groups using Dunnett's multiple comparisons procedure following significant one way analysis of varience.

Drugs are suspended in 1% methyl cellulose.

2. MES TEST

The maximal electroshock seizure (MES) threshold test in rodents is particularly sensitive for detecting potential anticonvulsant properties[1]. In this model, anticonvulsant agents elevate the threshold to electrically-induced seizures whilst proconvulsants lower the seizure threshold.

Method

Mice (male, Charles River, U.K. CD-1 strain, 25–30 g) are randomly assigned to groups of 10–20 and dosed orally or intraperitoneally at a dose volume of 10 ml/kg with various doses of compound (0.3–300 mg/kg) or vehicle. Mice are then subjected at 30 or 60 min post dose to a single electroshock (0.1 sec, 50Hz, sine wave form) administered via corneal electrodes. The mean current and standard error required to induce a tonic seizure in 50% ($CC_{50}$) of the mice in a particular treatment group is determined by the 'up and down' method of Dixon and Mood (1948)[2]. Stastical comparisons between vehicle- and drug-treated groups are made using the method of Litchfield and Wilcoxon (1949)[3].

In control animals the $CC_{50}$ is usually 14–18 mA. Hence the first animal in the control group is subjected to a current of 16 mA. If a tonic seizure does not ensue, the current is increased for a subsequent mouse. If a tonic convulsion does occur, then the current is decreased, and so on until all the animals in the group have been tested.

The percentage increase or decrease in $CC_{50}$ for each group compared to the control is calculated.

Studies are carried out using a Hugo Sachs Electronik Constant Current Shock Generator with totally variable control of shock level from 0 to 300 mA and steps of 2 mA are usually used.

Drugs are suspended in 1% methyl cellulose.

References

1. Loscher, W. and Schmidt, D. (1988). Epilepsy Res., 2, 145–181
2. Dixon, W. J. and Mood, A. M. (1948). J. Amer. Stat. Assn., 43, 109–126
3. Litchfield, J. T. and Wilcoxon, F.(1949). J. Pharmacol. exp. Ther., 96, 99–113

Results

The compound of example 6 enhanced seizure threshold by 84% at 30 mg/kg p.o.

3. X-Maze

The compounds of formula (I) or pharmaceutically acceptable salts thereof may be tested for therapeutic utility using the procedure outlined as follows:

Introduction

The X-maze test of anxiety (Handley and Mithani, 1984) examines the exploratory response of naive rats in an environment which offers both anxiogenic (open arms) and relatively non-anxiogenic (closed arms) areas. A selective increase in exploration of the open arms following drug pretreatment is therefore postulated to indicate anxiolytic effects.

Method

The X-maze was raised 70 cm above the floor and consisted of two enclosed arms 45 cm (long)×15 cm (wide) ×10 cm (high) and two open arms 45×10×1 cm arranged such that the two arms of each type were opposite each other. Both arm types are marked into two equal sections. Rats are placed onto the centre of the X-maze and observed for a period of 10 minutes during which time the following parameters were recorded: 1) the number of entries onto, and the time spent on, (a) open arms, (b) closed arms, (c) end of open arms and (d) end of closed arms. 2) the number of sections crossed. The fear-drive evoked in the open arms exceeds that in the enclosed arms and rats typically show a clear preference for the enclosed arms. Anxiolytic drugs increase the number of entries made onto, and the time spent on, the outer half of the open arms, and also the percentage of entries made onto, and the time spent on, the whole of the open arms. These four measures of anxiety, and also the total number of sections traversed, were calculated for each animal. Drugs are administered intraperitoneally or orally to groups of 6 to 12 rats 30 to 60 mins before testing. Statistical comparisons between vehicle- and drug-treated groups were made using a Mann-Whitney 'U' test (two tailed).

S. L. Handley and S. Mithani, Arch. Pharmacol., 1984 327 1–5

4. Mongrel Dog Delayed Cerebral Vasospasm

The compounds of formula (I) including cis-4-benzoylamino-6-cyano-3,4-dihydro-2,2-dimethyl-2H-benzo[b]pyran-3-ol or pharmaceutically acceptable salts thereof may be tested for therapeutic utility using the procedures outlined as follows:

Twenty-five male mongrel dogs, weighing 9–12 kg, are used in these studies. The animals are housed and cared for in accordance with the Guide for the Care and Use of Laboratory Animals [DHEW (DHHS) publication No. (NIH) 85–23, revised 1985]. All procedures using laboratory animals are approved by the Institutional Animal Care and Use Committee of SmithKline Beecham Pharmaceutical. Each animal is anaesthetized with pentobarbital (35 mg/kg, iv) and placed on a heated operating table in the supine position. All animals are then tracheotomized, paralyzed (tubocurarine; 0.1 mg/kg, i.v.) and artificially ventilated with room air. End-tidal $CO_2$ (et $CO_2$) is monitored continuously and arterial blood gas analysis was performed periodically to assure stable and adequate ventilation throughout each experiment. Polyethylene cannulae are placed in the left external jugular vein and the right femoral artery and vein for drug administration, monitoring arterial blood pressure, and blood sampling, respectively. Transfemoral catheterization of the left vertebral artery is then performed via the left femoral artery using a 5 french Lehman dacron catheter ( Bard, Tewksbury Mass.). Anaesthesia is supplemented as needed with pentobarbital (5 mg/kg, i.v.) prior to the experimental period.

The effects of the compounds of this invention on acute cerebral vasospasm are evaluated in 15 dogs. In all animals a control digital subtraction angiogram of the anterior spinal artery and basilar artery is obtained following the intravertebral injection of radiocontrast material (Omnipaque 300). In each dog, 4 mls of cerebrospinal fluid is then removed from the dorsal cistern via needle puncture of the atlantooccipital membrane and 4 mls of autologous venous blood was injected. An angiogram is then repeated in each dog 30 minutes following the intracisternal administration of blood and an acute vasospasm of the basilar and anterior spinal arteries is identified and quantitated. The infusion of vehicle (10% polyethylene glycol 200) for 30 minutes has no effect on the acute vasospasm. The effect of a 30 minute infusion of test compounds on the reversal of acute vasospasm is observed in the basilar and anterior spinal arteries.

The effects of the compounds of this invention are also examined in the chronic canine model of delayed cerebral vasospasm (two haemorrhage model of cerebral vasospasm). In this model, a control vertebral angiogram is obtained and autologous blood is administered intracisternally on day 1 (as above). On day 3 the intracisternal administration of blood is repeated and the severe delayed vasospasm is quantitated angiographically on day 7 in all animals. The infusion of vehicle (10% polyethylene glycol 200) for 60 minutes has no effect on the delayed vasospasm observed in the basilar and anterior spinal arteries (n=5). The effect of an infusion of test compounds on the reversal of significantly delayed cerebral vasospasm indicates that the compound is active.

5. The compounds of formula (I) or pharmaceutically acceptable salts thereof may be tested for therapeutic utility using the procedures outlined as follows:

1) Anti-Parkinsonian Activity

6- Hydroxydopamine-lesioned rat model

The above test as described by Ungerstedt, U. 1971, Acta Physiol. Scand 367, 49–68, and/or Ungerstedt, U, 1971, Acta Physiol Scand. 367, 69–93, may be used to determine the anti-Parkinsonian activity of compounds of formula(I) or pharmaceutically acceptable salts thereof.

2) Anti-Psychotic Activity

Amphetamine-induced rat hyperlocomotion model

The above test as described by Kokkindis L, and Anisman, M, 1980, Psychological Bulletin, 88, 551–579, may be used to determine the anti-psychotic activity of compounds of formula (I) or pharmaceutically acceptable salts thereof.

3) Anti-Migraine Activity

Cortical Spreading Depression and Migraine

The above test as described by Wahl et al, 1987, Brain Research, 411, 72–80 may be used to determine the anti-migraine activity of compounds of formula (I) or pharmaceutically acceptable salts thereof.

4) Cerebral ischaemia a) Mongolian Gerbil Test

The in vivo experiments are carried out on adult Mongolian gerbils (Tumblebrook Farm (Mass.). weighing 60–80 g. Transient forebrain ischemia is produced by bilateral carotid artery ligation under 2.5% isoflourane in 100% $O_2$ anesthesia, the animals being placed onto a heating pad to maintain body temperature at 37° C. The common carotid arteries are exposed and aneurism clips are placed on both arteries for a certain period of time indicated in the figure legends. PBN dissolved in saline was administered intraperitoneally as a bolus 30 min before occlusion (pretreatments) or immediately after and again at 6 h of reperfusion, followed by the same dose b.i.d. for 2 days (post-treatment). For quantification of CA1 neurons, animals are sacrificed at 7 days postischemia and perfused with buffered formalin. Brains were removed, stored in formalin for 3 days, embedded in paraffin, cut at 7$\mu$m-thick coronal sections (1.5–1.9 mm posterior to bregma[15]) and stained with thionin. The number of intact neurons over a 750-$\mu$m length of the CA1 layer on both hippocampal sides of 3 sections is counted for each animal.

b) MCAO Method

Three strains of mature male rats (SHR) are obtained from commercial vendors (Taconic Farms, Germantown, N.Y.; Charles River, Danyers, Mass.; and Charles River, respectively) at 18 wk of age (250–300 g in weight) and are housed for 2 to 4 weeks prior to utilization in these studies. In order to verify that the strains of animals studied are indeed hypertensive and normotensive, groups of animals from each strain are anesthetized with 2% isoflourane (Anaquest, Madison, Wis.) and chronically prepared under aseptic conditions for recording of blood pressure. The femoral artery is cannulated with polyethylene tubing (PE60; Clay Adams. Parsippany, N.J.) extending just into the descending aorta. The tubing is lead subdermally from the artery and exteriorized between the scapula just below the back of the neck and cleared/filled with sterile isotonic saline. Incisions are closed using 2–0 silk suture and treated with 5% lidocaine ointment (Astra Pharmaceuticals, Westborough, Mass.) Animals recover from surgery/ anesthesia within 5 min. Mean arterial blook pressures are recorded 4 to 5 h after surgery for 5 min/rat by connecting the exteriorized tubing in each rat to a Statham pressure transducer (P2.3Db; Statham Medical Instruments. Los Angeles, Calif.) with output to a polygraph (Model R711: Beckman Instruments, Inc., Fullerton, Calif.).

Focal Stroke Procedure

MCAO or sham surgery is carried out in the SHR, SD rats under sodium pentobarbital (65 mg/kg, i.p. and supplemented as needed) anesthesia. All animals are allowed free access to food and water prior to and after surgery. Body temperature is maintained at 37° C. using a heating pad throughout the surgical procedure. Surgery is conducted similar to that described previously (2.4). The right dorsal surface to the head and shaved and prepped with providone-iodine, and the rat placed in a stereotaxic device (David Kopf Instruments, Tujunga, Calif.) with the surgery (right) side of the head superior. A 1–2 cm incision was made between the orbit and the external auditory canal. The temporal muscle is dissected from the skull and retracted without damaging the zygomatic bond or mandibular nerve. Under an operating microscope and with saline irrigation, a 2–3 mm craniotomy is made just rostral to the zygomatic-squamosal skull suture. The dura is opened over the artery using the modified tip of a 30-gauge needle. For permanent right MCAO, using electrocoagulation (Force 2 Electrosurgical Generator, Valley Lab Inc., Boulder, Colo.), the artery was stimultaneously occluded and cut dorsal to the lateral olfactory tract at the level of the inferior cerebral vain. A small piece of sterile saline-soaked Gelfoam (Upjohn, Kalamazoo, Mich.) is then positioned over the craniotomy and the temporails muscle and skin are closed in two layers. Animals are allowed to recover from anesthesia under a heating lamp and then are returned to their cages. The animals are sacrificed 24 hours following MCAO and the brains are prepared from reactive histologic examination.

Measurements of Ischemic Damage

Following the neurologic evaluation (24 hours after surgery) rats are euthanized with an overdose of sodium pentobarbital. Within 2–3 min, brains are removed and six coronal forebrain slices (2 mm thick) are made from the level of the olfactory bulbs to the cortical-cerebellar junction using a rat brain slicer [(59); Zivic-Miller Laboratories Inc., Allison Park, Pa.]. These forebrain slices then are immersed immediately in a 1% solution of triphenyltetrazolium chloride (TTC) in phosphate buffer at 37° C. for 20–30 min (6.78). Strained tissues then are fixed by filtration in 10% phosphate buffered formalin. The two sides of each TTC-strained section are photographed in colour using a polaroid camera. These photographs are analyzed for the quantification of ischemic damage using an image analysis system (Amersham RAS 3000; Loats Associates, Inc.). Morphological changes following surgery are evaluated in the entire forebrain (total of 11 planar surfaces) for each animal. The 11 planar images are planar surfaces) for each animal. The 11 planar images were obtained from each side of the six 2 mm thick sections and correspond approximately to 1 mm section surfaces from +5 mm to −5 mm from bregma (97) and include the complete forebrain. These planar image surfaces (from the photographs) are digitized and used in the Image Analysis System for planimetry determination of infarct size and swelling. Two parameters of ischemic damage due to MCAO are determined for each slice as described previously (2,4,98,122). "Hemispheric swelling" is expressed as the percent increase in size of the ipsilateral (i.e., surgery side) hemisphere over the contralateral (normal) hemisphere and is calculated as:

$$\text{Percent Hemispheric Swelling} = \frac{\text{Ipsilateral Hemisphere Area} - \text{Contralateral Hemisphere Area}}{\text{Contralateral Hemisphere Area}} \times 100$$

"Infarct size" which was expressed as the percent infarcted tissue in reference to the contralateral (normal) hemisphere and is calculated as:

$$\text{Percent Hemisphere Infarct Size} = \frac{\text{infarct area}}{\text{Contralateral Hemisphere Area}} \times 100$$

The swelling and infarct size are expressed in reference to the contralateral hemisphere (i.e., ipsilateral ischemic damage is normalized to the normal contralateral hemisphere). These parameters are determined for each slice to evaluate the profile of damage throughout the forebrain (i.e., "forebrain profile") and for "total" forebrain changes by using the sum of all individual slice data in these formulas. The occurrence of brain edema asociated with hemispheric swelling following MCAO was determined by comparison of wet/dry weight as described previously (45,118). Rats were sacrificed by an overdose of sodium pentobarbital 24 hours after sham or MCAO surgery. The brains are quickly removed, the forebrain isolated at the cerebellar cortical junction and cut into two hemispheres, and each forebrain hemisphere measured on a Mettler Types H5 chemical balance (Mettler Instruments Corp, Hightstown, N.J.) within 2 min after decapitation. The dry weight was measured on the same scale after drying the hemisphere in an over at 80° C. for 48–72 hours. The water content of each hemisphere was calculated as the difference between the wet and dry weight as a percent fraction from the wet weight:

$$\text{Percent Water Content} = \frac{\text{Wet Weight} - \text{Dry Weight}}{\text{Wet Weight}} \times 100$$

We claim:

1. A compound which is trans-6-Acetyl-4-(3-azidobenzoylamino)-3,4-dihydro-8-iodo-2,2-dimethyl-2H-1-benzopyran-3-ol.

2. A compound which is trans-8-Bromo-4-(3-bromo4-fluorobenzoylamino)-6-ethyl-3,4-dihydro-2,2-dimethyl-2H-1-benzopyran-3-ol.

3. A compound which is trans-6-Acetyl4S-(3-azidobenzoylamino)-3,4-dihydro-8-iodo-2,2-dimethyl-2H-1-benzopyran-3R-ol.

4. A compound which is trans 6-Acetyl4-(4-fluorophenylbenzoylamino)-3,4-dihydro-2,2-dimethyl-8-(2-phenylethyl)-2H-1-benzopyran-3-ol.

5. A compound which is trans 6-Acetyl-4-(4-fluorophenylbenzoylamino)-3,4-dihydro-2,2-dimethyl-8-(2-phenylethenyl-)-2H-1-pyran-3-ol.

6. A compound which is (±)-10-bromo-2,2-dimethyl-trans4-(4-fluorobenzoylamino)-3,4,6,7,8,9-hexahydro-6-oxo-naphthaleno[3,2-b]pyran-3-ol.

7. A compound which is trans-3R,4S-6-Acetyl-4-(3-ethoxymethylbenzoylamino)-3-4-dihydro-8-iodo-2,2-dimethylben°[b]pyran-3-ol.

8. A compound which is trans-3R,4S-6-Acetyl-4-(3-Acetyloxymethylbenzoylamino)-3,4-dihydro-8-iodo-2,2dimethylbenzol[b]pyran-3-ol.

9. A compound which is trans-3R,4S-6-Acetyl-3,4-dihydro-4-(3-hydroxymethylbenzoylamino)-8-iodo-2,2-dimethylbenzo[b]pyran-3-ol.

10. A compound which is (±)-2,2-dimethyl-trans-4-(3-chloro4-fluorobenzoylamino-3,4,6,7,9,9-hexahydro-6-oxo-naphthaleno[3,2-b]pyran-3-ol.

11. A compound which is cis 6-Acetyl4S-(3-chlorobenzoylamino)-3,4-Dihydro-2,2-dimethyl-8-hydroxymethyl-2H-benzol[b]pyran-3S-ol.

12. A compound which is cis 8-Acetoxymethyl-6-acetyl4S-(3-chlorobenzoylamino)-3,4dihydro-2,2-dimethyl-2H-benzo[b]pyran-3S-ol.

13. A method of treatment of anxiety, mania, depression, the effects associated with withdrawal from substances of abuse, a disorder treatable and/or preventable with anticonvulsive agents, Parkinson's disease, psychosis, migraine, cerebral ischaemia, schizophrenia, OCD, a panic disorder and/or agression in a sufferer, comprising administering to the sufferer in need thereof an effective amount of a compound selected from the group consisting of:

trans-6-Acetyl4-(3-azidobenzoylamino)-3,4-dihydro-8-iodo-2,2-dimethyl-2H-1-benzopyran-3-ol;

trans-8Bromo-4-3-bromo-4-fluorobenzoylamino-6-ethyl-3,4-dihydro-2.2-dimethyl-2H-1-benzopyran-3-ol;

trans-6-Acetyl-4S-(3-azidobenzoylamino)-3,4-dihydro-8-iodo-2,2-dimethyl1-2H-1-benzopyran-3R-ol;

trans 6-Acetyl4-(4-fluorophenylbenzoylamino)-3,4-dihydro-2,2-dimethyl-8-(2-phenylethyl)-2H-1-benzopyran-3-ol;

trans 6-Acetyl-4-(4-fluorophenylbenzoylamino -3,4-dihydro-2,2-dimethyl-8-(2-phenylethenyl)-2H-1-benzopyran-3-ol;

(±)-10-bromo-2,2-dimethyl-trans-4-(4-fluorobenzoylamino)-3,4,6,7,8,9-hexahydro-6-oxo-naphthaleno[3,2-b]pyran-3-ol;

trans-3R,4S-6-Acetyl4-(3-ethoxymethylbenzoylamino)-3-4-dihydro-8-iodo-2,2-dimethylbenzo[b]pyran-3-ol;

trans-3R,4S-6-Acetyl4-(3-Acetyloxymethylbenzoylamino)-3,4dihydro-8-iodo-2,2dimethylbenzo[b]pyran-3-ol;

trans-3R,4S-6-Acetyl-3,4-dihydro-4-(3-hydroxymethylbenzoylamino)-8-iodo-2,2-dimethylbenzo[b]pyran-3-ol;

(±)-2,2-dimethyl-trans-4-(3-chloro-4-fluorobenzoylamino-3,4,6,7,8,9-hexahydro-6-oxo-naphthaleno[3,2-b]pyran-3-ol;

cis 6-Acetyl-4S-(3-chlorobenzoylamino)-3,4-Dihydro-2,2-dimethyl-8-hydroxymethyl-2H-benzol[b]pyran-3S-ol: or cis 8-Acetoxymethyl-6-acetyl4S-(3-chlorobenzoylamino)-3,4dihydro-2,2-dimethyl-2H-benzo[b]pyran-3S-ol or a pharmaceutically acceptable salt thereof.

14. A pharmaceutical composition comprising a compound selected from the group consisting of:

trans-6-Acetyl-4-(3-azidobenzoylamino)-3,4-dihydro-8-iodo-2,2-dimethyl-2H-1-benzopyran-3-ol;

trans-8-Bromo-4-(3-bromo-4-fluorobenzoylamino)-6-ethyl-3,4-dihydro-2,2-dimethyl-2H-1-benzopyran-3-ol;

trans-6-Acetyl-4S-(3-azidobenzoylamino)-3,4-dihydro-8-iodo-2,2-dimethyl-2H-1-benzopyran-3R-ol;

trans 6-Acetyl-4-(4-fluorophenylbenzoylamino)-3,4-dihydro-2,2-dimethyl-8-(2-phenylethyl)-2H-1-benzopyran-3-ol;

trans 6-Acetyl-4-(4-fluorophenylbenzoylamino)-3,4-dihydro-2,2-dimethyl-8-(2-phenylethyl)-2H-1-benzopyran-3-ol;

(±)-10-bromo-2,2-dimethyl-trans-4-(4-fluorobenzoylamino)-3,4,6,7,8,9-hexahydro-6-oxo-naphthaleno[3,2-b]pyran-3-ol;

trans-3R,4S-6-Acetyl-4-(3-ethoxymethylbenzoylamino)-3-4-dihydro-8-iodo-2,2-dimethylbenzo[b]pyran-3-ol;

trans-3R,4S-6-Acetyl-4-(3-Acetyloxymethylbenzoylamino)-3,4-dihydro-8-iodo-2,2dimethylbenzo[b]pyran-3-ol;

trans-3R,4S-6-Acetyl-3,4dihydro-4-(3-hydroxymethylbenzoylamino)-8-iodo-2,2-dimethylbenzo[b]pyran-3-ol;

(±)-2,2-dimethyl-trans4-(3-chloro-4-fluorobenzoylamino-3,4,6,7,8,9-hexahydro-6-oxo-naphthaleno[3,2-b]pyran-3-ol;

cis 6-Acetyl-4S-(3-chlorobenzoylamino)-3,4-Dihydro-2,2-dimethyl-8-hydroxymethyl-2H-benzo[b]pyran-3S-ol; or cis 8-Acetoxymethyl-6-acetyl4S-(3-chlorobenzoylamino)-3,4dihydro-2,2-dimethyl-2H-benzo[b]pyran-3S-ol or a pharmaceutically acceptable salt thereof and a pharmaceutically acceptable carrier.

15. The method of claim 13 wherein said substances of abuse are cocaine, nicotine, alcohol and benzotriazines.

16. The method of claim 13 wherein said disorder treatable and/or preventable with anti-convulsive agents is epilepsy.

* * * * *